United States Patent
Isaguliants et al.

(10) Patent No.: US 7,087,782 B2
(45) Date of Patent: Aug. 8, 2006

(54) PROCESS FOR THE PREPARATION OF ACROLEIN AND/OR ACRYLIC ACID

(75) Inventors: Georgij Vacheevich Isaguliants, Mosva (RU); Inna Pavlovna Belomestnykh, Mosva (RU); Søren Dahl, Hillerød (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 11/113,104

(22) Filed: Apr. 25, 2005

(65) Prior Publication Data

US 2005/0261522 A1   Nov. 24, 2005

(30) Foreign Application Priority Data

May 5, 2004  (DK) .............................. 2004 00715

(51) Int. Cl.
C07C 51/16 (2006.01)
C07C 45/00 (2006.01)

(52) U.S. Cl. ..................................... 562/549; 568/475
(58) Field of Classification Search ................ None
See application file for complete search history.

(56) References Cited

U.S. PATENT DOCUMENTS

| 4,499,301 A | 2/1985 | Murib |
| 5,380,933 A | 1/1995 | Ushikubo et al. |
| 6,160,162 A | 12/2000 | Karim et al. |
| 6,504,053 B1 | 1/2003 | Chaturvedi et al. |
| 6,541,664 B1 | 4/2003 | Jachow et al. |
| 6,624,111 B1 | 9/2003 | Chaturvedi et al. |
| 6,700,015 B1 | 3/2004 | Chaturvedi et al. |

FOREIGN PATENT DOCUMENTS

| EP | 0 117 146 A1 | 8/1984 |
| EP | 1 080 784 | 3/2001 |

Primary Examiner—Paul A. Zucker
(74) Attorney, Agent, or Firm—Dickstein Shapiro Morin & Oshinsky LLP

(57) ABSTRACT

Process for the preparation of acrolein and/or acrylic acid by catalytic gas-phase selective oxidation reaction of propane, the process comprising contacting a reaction gas containing propane and an oxygen-containing gas over a mixed metal oxide solid catalyst supported on a $TiO_2$—$MoO_3$ porous support.

10 Claims, 1 Drawing Sheet

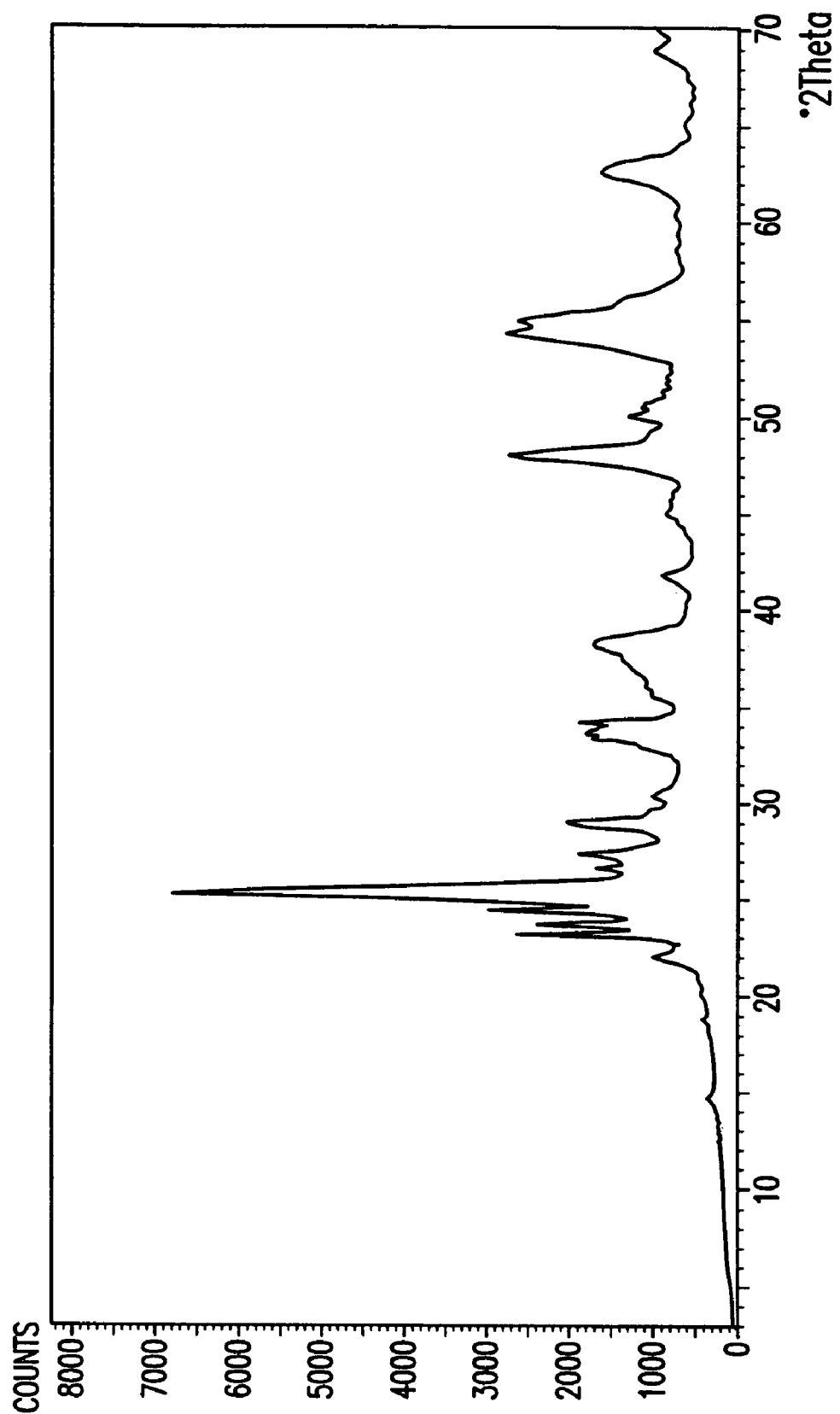

PROCESS FOR THE PREPARATION OF ACROLEIN AND/OR ACRYLIC ACID

The invention relates to a process for the preparation of acrolein and/or acrylic acid by catalytic gas-phase selective oxidation of propane. In particular, the process relates to conversion of a reaction gas containing propane and molecular oxygen and optionally inert components over a mixed metal oxide solid catalyst supported on a $TiO_2$—$MoO_3$ porous support.

BACKGROUND OF THE INVENTION

Acrolein and acrylic acid are produced in large scale for use as chemical building blocks mainly for producing polymers. The totally dominating process for production of acrolein and/or acrylic acid is today a gas-phase oxidation of propene, see for instance Ullmann's Encyclopedia of Industrial Chemistry, Release 2002, $6^{th}$ edition. In view of the price difference between propene and propane and as propene is used as feedstock for producing many other products, it would be advantageous to have a competitive process, which uses propane instead of propene as raw material for preparing acrolein and acrylic acid.

EP patent application No. 117146 proposes preparing acrolein and/or acrylic acid from propane by a two-stage process, where propane is subjected to a partial oxydehydrogenation with molecular oxygen in the first stage to give propene. The product gas from the first stage is then used directly for the preparation of acrolein and acrylic acid by gas-phase catalytic propene oxidation in the second stage. A disadvantage of this and similar processes is that the reaction has to be carried out in two reactors operating at different reactions conditions.

Processes for converting propane into acrolein and/or acrylic acid in a single reactor are also known. U.S. Pat. No. 6,541,664 proposes a process, where two different catalysts are loaded spatially in succession into the same reactor. The first catalyst helps transforming propane into propene, which is then converted to acrolein and/or acrylic acid over the second catalyst.

Similar processes where the trouble of producing and loading two different catalysts is avoided have also been suggested. U.S. Pat. No. 5,380,933 describes catalysts containing Mo, V and Te oxide that are able to accomplish this, and a number of patents describe subsequent modifications of this catalyst system, see for instance U.S. Pat. Nos. 6,160,162, 6,504,053, 6,624,111 and 6,700,015. This catalyst system has the disadvantage that the catalyst contains Te and this component might be considered undesirable because it is known to be toxic and volatile. Even though the ecological problem can be handled the long time stability of these catalysts will be limited.

SUMMARY OF THE INVENTION

It is the object of the present invention to provide a process for converting propane into acrolein and/or acrylic acid by selective oxidation using molecular oxygen as oxidant over a supported mixed metal oxide catalyst. This process does not have the disadvantages of the above-mentioned methods described in the prior art. The process of the invention has the advantage to having high selectivity to acrolein and/or acrylic acid.

BRIEF DESCRIPTION OF THE DRAWINGS

The sole drawing shows the powder X-ray diffraction pattern of the catalyst preferred for use in the present invention.

DETAILED DESCRIPTION OF THE INVENTION

The present invention provides a process for the catalytic gas-phase oxidation of propane to acrolein and/or acrylic acid, in which a reaction gas containing propane and molecular oxygen and optionally inert components is passed over a mixed metal oxide solid catalyst supported on a $TiO_2$—$MoO_3$ porous support. Preferably, the mixed metal oxide contains vanadium, tungsten, antimony and bismuth and has the empirical formula

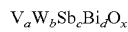

wherein x is determined by the oxidation state of the metals and the coefficients a,b,c,d can be any number larger than or equal to 0.

By the term "mixed metal oxide" is meant an oxide containing different metals. If the oxide contains vanadium, tungsten, antimony and bismuth as given by the empirical formula above, then the metal oxide can also be represented by a particular oxide weight ratio of:

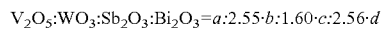

A specific crystal structure of the catalyst is most preferred. Specifically, preference is given to those catalysts, which have a powder X-ray diffraction (XRD) pattern similar to the one shown in the figure.

Preparing acrolein and/or acrylic acid using the mixed metal oxide catalyst supported on a $TiO_2$—$MoO_3$ porous support shows a larger conversion of propane and improved selectivity and yield of these two products.

The catalyst can be prepared in the following manner:

Firstly, a $TiO_2$—$MoO_3$ support or a support precursor for $TiO_2$—$MoO_3$ is made by any suitable chemical procedure. Most preferred is a sol-gel method. Secondly, the support or support precursor mixture is mixed with metal oxide precursors (as powders and/or in solution) in the ratio required. Optionally this material can be used to form a slurry by adding a liquid such as water and other materials such as a silica sol. This material is dried by an appropriate method such as spray drying, evaporation to dryness and vacuum drying. Spray drying is preferred. This dried material may be further heated to a temperature between 200° C. and 800° C. in a flow of a suitable gas mixture. The most preferred gas mixture is air and the most preferred temperature is 400–600° C.

The catalyst obtained by the above-mentioned method may be used as the final catalyst. It can, however, also be formed into a catalyst together with a suitable material such as silica, alumina, titania, aluminosilicate, zirconia or similar materials. Furthermore, it may be moulded into a suitable shape and particle size depending on the scale or system of the reactor used in the process.

The $TiO_2$—$MoO_3$ support used in the catalyst has a composition of 60–90 mole % $TiO_2$ and 10–40 mole % $MoO_3$. A preferable embodiment of the invention includes a catalyst with a support with the composition 80 mole % $TiO_2$ and 20 mole % $MoO_3$.

The process for catalytic gas-phase oxidation of propane to acrolein and/or acrylic acid comprises contacting a gas containing propane and oxygen, preferably supplied as air, and optionally inert components. Nitrogen, carbon dioxide and steam are the preferred inert components. The purity of the propane is not particularly limited and propane containing impurities such as, methane, ethane, air or carbon dioxide do not interfere with the process. The preferred molar ratio between propane and oxygen is 0.1–10 and more preferably 0.5–2.

The oxygen-containing gas suitable for the selective oxidation reaction of propane can be molecular oxygen or air.

Optionally propane can be reacted by contacting with the catalyst in the absence of gas phase molecular oxygen. In such a case the catalyst has to be contacted with oxygen containing gas from time to time in order to regenerate the catalyst before it can be reused for the conversion of propane.

The reactor used for the reaction may be a fixed bed or a fluidised bed reactor. As the reaction is an exothermic reaction fluidised bed reactors or cooled fixed bed reactors are preferred in order to allow sufficient control of the reaction temperature. The preferred reaction temperature is 200–500° C. and more preferably 300–500° C. The preferred pressure for conducting the reaction is 0.5–15 atm, and more preferably at atmospheric pressure or slightly above atmospheric pressure.

During the oxidation reaction not all propane is converted to acrolein and/or acrylic acid. Some propane is converted to by-products such as carbon monoxide, carbon dioxide, acetic acid and some of the propane is left unconverted. A separation procedure is therefore conducted after the reaction step where most of the acrolein and/or acrylic acid are isolated optionally with some of the by-products. The separation is for instance done via cooling whereby the products are liquefied while propane is in the gas phase. The rest or part of the stream containing the propane is returned to the reactor. Optionally some purification of the stream can take place in order to increase the concentration of propane.

The following examples are illustrative for the present invention and are not to be considered as limiting. In the examples the conversion of propane and the selectivity and yield of acrolein and acrylic acid have been studied.

The conversion, selectivity and yield are represented by the following formulas:

$$\text{Conversion (\%)} = \frac{\text{Moles of propane consumed} \times 100}{\text{Moles of propane supplied}}$$

$$\text{Selectivity (\%)} = \frac{\text{Moles of (acrolein and acrylic acid) produced} \times 100}{\text{Moles of propane consumed}}$$

$$\text{Yield (\%)} = \frac{\text{Moles of (acrolein and acrylic acid) produced} \times 100}{\text{Moles of propane supplied}}$$

EXAMPLES

Example 1

Preparation of $TiO_2$ (80 mole %)—$MoO_3$ (20 mole %) Support

To 20 ml of ice-cooled water, 9.5 ml of liquid titanium tetrachloride were gradually added under stirring and cooling to prepare a clear, solution. Thereto a, homogeneous solution of 3.81 g of ammonium heptamolybdate in 150 ml of water was added drop-wise over a period while stirring. To the obtained transparent liquid were slowly added 28% aqueous ammonia solution (28 ml) under vigorous stirring until a gel was formed (pH~7). After addition of 300 ml of distilled water and agitation the formed gel was left over night to age.

Further the gel was carefully washed four times with 300 ml of water in order to remove the ammonium chloride formed during interaction of ammonia with titanium tetrachloride.

The washed gel was stored in an open beaker for 24 hours to complete the aging and then heated for 3 hours at 100° C. under agitation to remove the major part of water and to form a white paste of support precursor. The support precursor consisted of $TiO_2$(80 mole %)—$MoO_3$(20 mole %).

This support was used as support in the mixed metal oxide catalysts prepared in Examples 2–12 illustrating the invention.

Preparation of a Mixed Metal Oxide (27 wt %) Catalyst on $TiO_2$ $MoO_3$ Support (73 wt %)

2.0 g of powdered ammonium vanadate and 1.5 g of ammonium tungstate together with 0.4 g of antimony trioxide and 0.8 g of bismuth nitrate were sequentially added to the support precursor paste obtained above and carefully mixed and heat-treated at 70° C. for two hours to obtain a material that could be moulded by extrusion. The mouldable material obtained was placed in a quartz tube and subjected to thermal treatment under airflow at 500° C. for 5–6 hours.

The sample thus obtained was a mixed metal oxide catalyst with a oxide weight ratio of $V_2O_5$:$WO_3$:$Sb_2O_3$:$Bi_2O_3$=4:3:1:1, and a BET surface area of 2 $m^2$/g. It was subjected to XRD analysis. The diffraction pattern is depicted in the figure. This figure shows that the preferred catalyst contains crystalline phases of $TiO_2$, $MoO_3$, $WO_3$, $V_2MoO_8$, $BiVO_4$ and $(Sb_{0.917}V_{0.917})O_4$.

A 2 g sample of the supported mixed metal oxide catalyst was placed in a quartz tube and heated at 400° C. in air flow and then examined for catalytic performance in propane oxidation. A feed mixture with a molar ratio propane:oxygen:nitrogen=4:4:92 was used at a reaction temperature of 400° C. and a space velocity of 1600 $h^{-1}$. The results are shown in Table 1.

Example 2

2 g of a catalyst prepared in the same manner as in Example 1 with an oxide weight ratio of $V_2O_5$:$WO_3$:$Sb_2O_3$:$Bi_2O_3$=3:8:9:1 were examined for catalytic performance in propane oxidation. A feed mixture with a molar ratio propane:oxygen:nitrogen=4:4:92 was used at a reaction temperature of 400° C. and a space velocity of 1600 $h^{-1}$. The results are shown in Table 1.

Example 3

2 g of a catalyst prepared in the same manner as in Example 1 where the weight ratio between the oxides and the $TiO_2$—$MoO_3$ support=3/2, i.e.:

(Weight of $V_2O_5$:$WO_3$:$Sb_2O_3$:$Bi_2O_3$)/(Weight of $TiO_2$—$MoO_3$)=3/2 was examined for the catalytic performance in propane oxidation. A feed mixture with a molar ratio propane:oxygen:-nitrogen=4:4:92 was used at a reaction temperature of 400° C. and a space velocity of 1600 $h^{-1}$. The results are shown in Table 1.

Example 4

2 g of a mixed metal oxide prepared in the same manner as in Example 1 were examined for the catalytic performance in propane oxidation. A feed mixture with a molar ratio propane:oxygen:nitrogen=4:4:92 was used at a reaction temperature of 380° C. and a space velocity of 1600 h$^{-1}$. The results are shown in Table 1.

Example 5

2 g of a mixed metal oxide prepared in the same manner as in Example 1 were examined for the catalytic performance in propane oxidation. A feed mixture with a molar ratio propane:oxygen:nitrogen=3:2:95 was used at a reaction temperature of 400° C. and a space velocity of 1600 h$^{-1}$. The results are shown in Table 1.

Example 6

2 g of a catalyst prepared in the same manner as in Example 1 with an oxide weight ratio of $V_2O_5$:$WO_3$:$Sb_2O_3$:$Bi_2O_3$=1:3:1:1 were examined for the catalytic performance in propane oxidation using a feed mixture with a molar ratio propane:oxygen:nitrogen=4:4:92. The reaction temperature was 400° C. and the space velocity was 1600 h$^{-1}$. The results are shown in Table 1.

Example 7

2 g of a catalyst prepared in the same manner as in Example 1 with an oxide weight ratio of $V_2O_5$:$WO_3$:$Sb_2O_3$:$Bi_2O_3$=4:3:1:0 were examined for the catalytic performance in propane oxidation using a feed mixture with a molar ratio propane:oxygen:nitrogen=4:4:92. The reaction temperature of was 400° C. and the space velocity was 1600 h$^{-1}$. The results are shown in Table 1.

Example 8

2 g of a mixed metal oxide prepared in the same manner as in Example 1 were examined for the catalytic performance in propane oxidation using a feed mixture with a molar ratio propane:oxygen:nitrogen=4:8:88. The reaction temperature was 400° C. and the space velocity was 1600 h$^{-1}$. The results are shown in Table 1.

Example 9

2 g of a mixed metal oxide prepared in the same manner as in Example 1 were examined for the catalytic performance in propane oxidation using a feed mixture with a molar ratio propane:oxygen:nitrogen=4:4:92. The reaction temperature was 400° C. and the space velocity was 2050 h$^{-1}$. The results are shown in Table 1.

Example 10

2 g of a mixed metal oxide prepared in the same manner as in Example 1 were examined for the catalytic performance in propane oxidation using a feed mixture with a molar ratio propane:oxygen:nitrogen=4:4:92 at a reaction temperature of 400° C. and a space velocity of 1000 h$^{-1}$. The results are shown in Table 1.

TABLE 1

| Example | Conversion of propane (%) | Selectivity to acrolein + acrylic acid (%) | Yield of acrolein + acrylic acid (%) |
|---|---|---|---|
| 1 | 21.0 | 80.0 | 16.8 |
| 2 | 47 | 15.3 | 7.2 |
| 3 | 33.0 | 18.0 | 5.9 |
| 4 | 9.8 | 77.8 | 7.6 |
| 5 | 10.7 | 80.6 | 8.6 |
| 6 | 38.3 | 16.3 | 6.2 |
| 7 | 29.6 | 15.2 | 4.5 |
| 8 | 21.3 | 47 | 9.9 |
| 9 | 12.4 | 82.8 | 10.2 |
| 10 | 25.7 | 58.4 | 15.0 |
| 11 | 15.0 | 11.5 | 1.8 |
| 12 | 20 | 5.7 | 1.1 |
| 13 | 28.9 | 8.4 | 2.4 |
| 14 | 14.4 | 32.1 | 4.6 |
| 15 | 13.5 | 57.5 | 7.8 |

Example 11

10 g of the $TiO_2$(80 mole %)—$MoO_3$(20 mole %) support precursor prepared in the same manner as in Example 1 were subjected to thermal treatment in airflow at 500° C. for 5–6 hours. The obtained black powder was sequentially impregnated with water solutions of 2 g of powdered ammonium vanadate and 1.5 g of ammonium tungstate together with 0.4 g of antimony trioxide suspended in a water solution of 0.8 g of bismuth nitrate. The obtained slurry was carefully mixed and heat-treated at 60–80° C. to obtain a black solid, which was then subjected to thermal treatment in airflow at 500° C. for 5–6 hours. The sample thus obtained had a weight oxide ratio as specified in Example 1 and was examined for the catalytic performance in propane oxidation as in Example 1. The results are shown in Table 1.

Example 12

2 g of a catalyst prepared in the same manner as in Example 1 except that the washed gel was stored in an open beaker for two weeks to complete the aging. Further it was treated and examined as in Example 1. The results are shown in Table 1.

Comparative Example 13

A mixture of commercial oxides of Ti, Mo, V, W, Sb and Bi oxide catalyst of same atom ratio as in Example 1 was mixed and ground in a mortar. This mixture was moulded by a tableting machine into tablets. After fragmentation these were treated and examined as in Example 1. The results are shown in Table 1.

Comparative Example 14

A mixed metal oxide catalyst with the empirical formula $Mo_1V_{0.3}Te_{0.23}Nb_{0.12}O_x$ where x is determined by the oxidation state of the metal component was prepared as follows:

15.7 g of ammonium metavanadate were dissolved in 325 ml of warm water, and 23.6 g of telluric acid and 78.9 g of ammonium paramolybdate were sequentially added thereto to obtain a uniform solution. Furthermore, 117.5 g of an aqueous solution of ammonium niobium oxalate having niobioum concentration of 0.456 mole/kg were mixed thereto to obtain a slurry. This slurry was heated to obtain a solid, which was calcined for two hours at 600° C.

A 2 g sample was placed in a quartz tube and after heating at 400° C. in air flow and then examined for the catalytic performance in propane oxidation using a feed mixture with a molar ratio propane:oxygen:nitrogen=4:15:81 at a reaction temperature of 400° C. and a space velocity of 1600 h$^{-1}$. The results are shown in Table 1.

Comparative Example 15

2 g of a catalyst prepared in the same manner as in Comparative Example 14 were placed in a quartz tube and after heating at 400° C. in air flow and then examined for the catalytic performance in propane oxidation using a feed mixture with a molar ratio propane:oxygen:water:nitrogen=4:20:64:76 at a reaction temperature of 380° C. and a space velocity of 1480 h$^{-1}$. The results are also shown in Table 1.

The invention claimed is:

1. Process for the preparation of acrolein and/or acrylic acid by catalytic gas-phase selective oxidation reaction of propane, the process comprising contacting a reaction gas containing propane and an oxygen-containing gas over a mixed metal oxide solid catalyst supported on a TiO$_2$—MoO$_3$ porous support.

2. Process according to claim 1, wherein the mixed metal oxide solid catalyst comprises V, W, Sb and Bi.

3. Process according to claim 2, wherein the mixed metal oxide solid catalyst has the empirical formula $V_aW_bSb_cBi_dO_x$, where x is determined by the oxidation state of the metals and the coefficients a,b,c,d can be any number larger than or equal to 0.

4. Process according to claim 1, wherein the TiO$_2$—MoO$_3$ support comprises 60–90 mole % TiO$_2$ and 10–40 mole % MoO$_3$.

5. Process according to claim 4, wherein the TiO$_2$—MoO$_3$ support comprises 80 mole % TiO$_2$ and 20 mole % MoO$_3$.

6. Process according to of claim 1, wherein the reaction gas contains inert components.

7. Process according to claim 1, wherein the selective oxidation reaction occurs at a temperature of between 200° C. and 500° C.

8. Process according to claim 1, wherein the selective oxidation reaction occurs at a pressure of 0.5–15 atm.

9. Process according to claim 1, wherein the molar ratio between propane and oxygen in the oxygen-containing gas is 0.1–10.

10. Process according to claim 9, wherein the molar ratio between propane and oxygen is and 0.5–2.

* * * * *